United States Patent [19]

Lyman et al.

[11] Patent Number: 4,927,764

[45] Date of Patent: May 22, 1990

[54] TISSUE CULTURE FLASK

[75] Inventors: George Lyman, Cape Porpoise; Gregory Mathus, Concord, both of Mass.

[73] Assignee: Costar Corporation, Cambridge, Mass.

[21] Appl. No.: 122,052

[22] Filed: Nov. 17, 1987

[51] Int. Cl.5 .......................... B01L 3/08; C12M 1/24
[52] U.S. Cl. ...................................... 435/296; 215/10; 215/31; 422/102; 435/284; 435/298
[58] Field of Search ................. 422/102; 435/284, 296, 435/298; 215/10, 31

[56] References Cited

U.S. PATENT DOCUMENTS 3,870,602  3/1975  Froman et al.
4,334,028  6/1982  Carver ............................ 422/102 X
4,770,854  9/1988  Lyman ............................ 422/102
4,851,351  7/1989  Akamine ......................... 436/296

Primary Examiner—Barry S. Richman
Assistant Examiner—Jill Johnston
Attorney, Agent, or Firm—Wolf Greenfield & Sacks

[57] ABSTRACT

A tissue culture flask having a flat bottom wall with optical properties on the inner surface of which cells are grown. A top wall opposite the bottom wall has a large opening therethrough which provides access to the growing surface for the removal of cells growing on the surface. The opening is closed by a flexible transparent film which is sealed to the top wall and which may be peeled off the top wall to provide access to the flask interior.

15 Claims, 3 Drawing Sheets

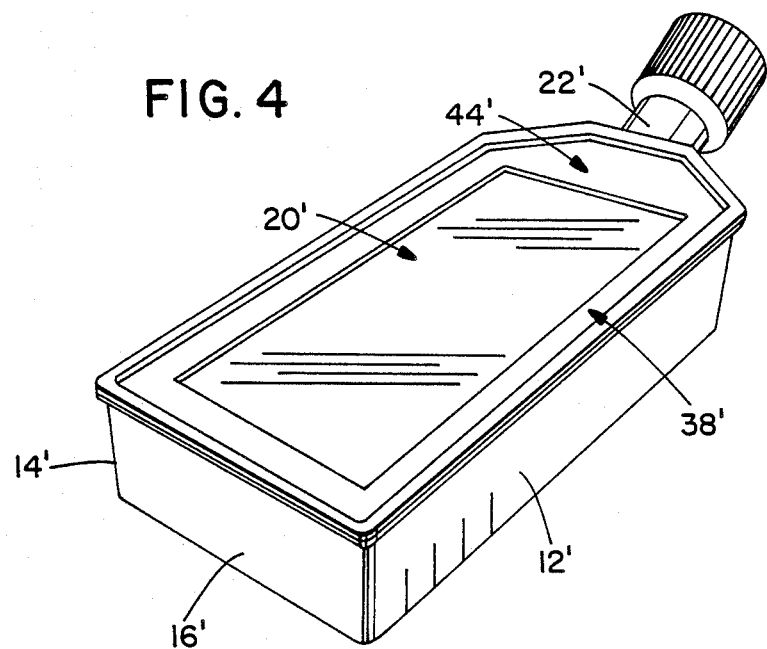
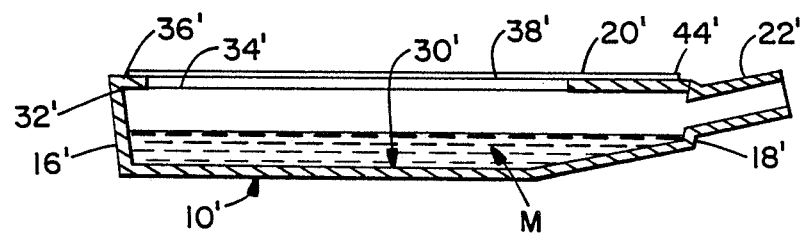
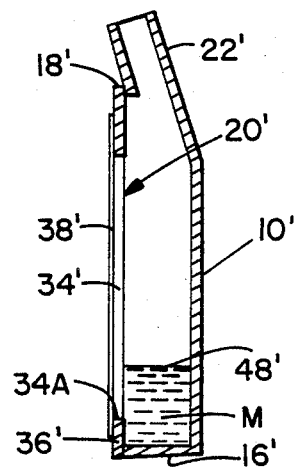

TISSUE CULTURE FLASK

INTRODUCTION

This invention relates to tissue culture flasks. The flask is particularly suitable for use in tumor research and for growing monolayers of skin cells.

Tissue culture flasks presently available all include threaded necks that provide the only means for introducing cells and media to the interior of the flasks and for removing tissue cultures from the inside. To facilitate removal of material from the flasks, various features have been developed including inclined ramps between the neck and growing surface and, specially formed necks which allow scrapers to reach all the corners of the growing surface. While these features make use of the flasks somewhat more convenient, it nevertheless remains difficult to remove material from the growing surface, particularly when only selected areas are to be removed for analysis, and it is essentially impossible to remove large sections of monolayers of skin cells suitable for grafting through the neck. To remove selected areas of the cultures or to remove large layers of skin cells, technicians now frequently cut the flasks open with a hot knife or other tool.

The prior art contains reference to a flask having a wall opposite the growing surface, which has a weakened area that may be broken away to provide access to the growing surface. This arrangement has many disadvantages, the most obvious of which are the costly molds required to manufacture the flasks and the possiblity of chips of plastic falling into the media or growing tissue within the flask.

The primary object of the present invention is to provide a tissue culture flask with an access opening to the growing surface which enables all areas of the growing surface to be reached most conveniently without special manipulation of scrapers or other tools through the flask neck.

Another important object of the present invention is to provide a removable closure for the top wall of a tissue culture flask, which enables the flask to be easily opened and which will not generate plastic particles or other debris when removed.

Another more general object of the present invention is to provide a tissue culture flask which is particularly suitable for use in growing monolayers of skin cells intended to be used as skin grafts.

To accomplish these and other objects, this invention comprises a flask having a large transparent bottom panel having optical properties, and a top wall opposite the bottom wall, which has a large opening to provide ready access to the growing surface on the bottom wall. The opening in the top wall is closed by a clear plastic film that may be peeled off the top wall when access is desired. The flask has a conventional neck closed by a cap, which neck provides access for seeding the flask and introducing media in which the cells may be cultured.

These and other objects and features of the present invention will be better understood and appreciated from the following detailed description of several embodiments thereof selected for purposes for illustration as shown in the accompanying drawings.

BRIEF FIGURE DESCRIPTION

FIG. 4 is a perspective view similar to FIG. 1 showing a second embodiment of this invention;

FIG. 5 is a cross-sectional view of the flask of FIG. 4 shown oriented in the normal position;

FIG. 6 is a cross-sectional view of the flask of FIG. 4 showing it standing on end in the position for filling;

DETAILED DESCRIPTION

Figure 1:
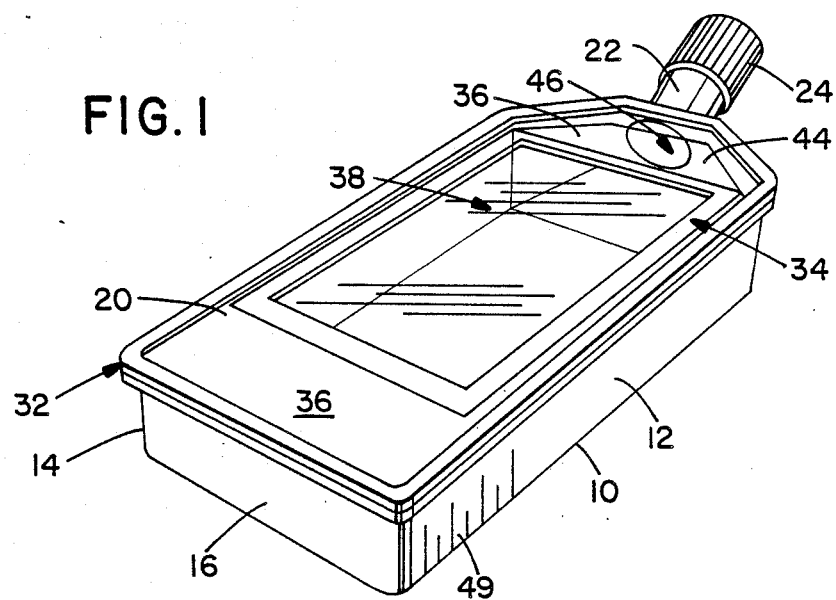
FIG. 1 is a perspective view of one embodiment of tissue culture flask constructed in accordance with this invention.
Figure 2:
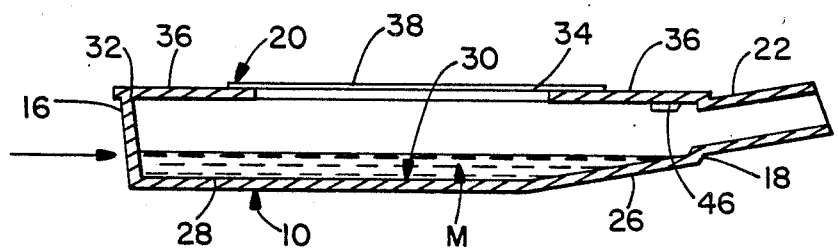
FIG. 2 is a vertical cross-sectional view through the flask of FIG. 1 oriented in the normal position and, with the cap removed.
Figure 3:
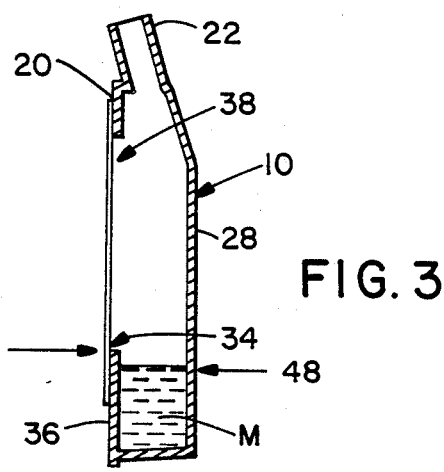
FIG. 3 is a vertical cross-sectional view similar to FIG. 2 but showing the flask standing on end, the position assumed when the flask is being filled.

The embodiment of flask shown in FIGS. 1–3 includes a bottom wall 10, side walls 12 and 14, end walls 16 and 18, and top wall 20. A neck 22 is secured to end wall 18, and the neck is threaded to receive cap 24. The bottom wall 10 includes a ramp 26 and a flat main panel 28 whose functions are described below.

In the embodiment shown, the bottom wall 10 side walls 12 and 14, end walls 16 and 18 and neck 22 which together comprise the base of the flask are molded as an integral unit of transparent material such as polystyrene, and panel 28 of bottom wall 10 has optical characteristics which allows distortion free viewing of the tissue cultures growing on the inner surface 30 of panel 28 when examined through the bottom wall. The top wall 20 is molded as a separate part of the same or similar material to that used in the base of the flask. The top wall 20 is ultrasonically welded to the base portion 10 about seam 32. While this seam is shown at the top of the side and end walls 12, 14, 16 and 18, it is apparent that the seam may be in any part of the side and end walls.

The top wall 20 is molded with an opening 34 which provides access to the growing surface 30 of panel 28 of bottom wall 10. The opening 34 is spaced inwardly from the peripheral edge of the top wall 20 so as to leave a flange 36 to which a clear plastic cover 38 is adhered. The clear flexible plastic cover 38 may be heat sealed to the flange 36 so that it can be peeled back to uncover the opening 34 and provide access to growing surface 30. Alternatively, a ribbon of pressure sensitive adhesive may be applied to the lower surface of the cover 38 about the opening 34 to secure the cover to the flange 36. The use of pressure sensitive adhesive will allow the cover to be resealed to the top wall if that is desirable for a particular application. Typically, the flexible clear plastic cover 38 may be made of polyester or nylon film.

It will be noted in FIG. 1 that the flexible plastic cover 38 is formed with a tab 44 at the end of the cover adjacent the neck 22 to facilitate gripping of the cover to peeled it from the top wall 20 when it is desired to remove the cover to provide access to the surface 30 of the bottom wall. In addition, a recess 46 may be molded in the portion of the top wall 20 which underlies the tab 44 to make it easier for the user to slip a finger under the tab so as to grip the cover and assist in peeling it off the cover of the top wall. If the width of the seal between the cover and top wall is small immediately adjacent the tab, it will make it easier for the user to start the separation or peeling action.

It will be noted in FIG. 3 that the opening 34 in top wall 20 is located above the fill level 48 of media M introduced to the flask through the neck 22. (In FIG. 1, it will be noted that a scale 49 is carried on side wall 12 to assist the user in measuring the volume of media poured into the flask.) Therefore, the cover 34 may not be hermetically sealed to the flange 36 of the top wall 20.

The embodiment of flask shown in FIGS. 1–3 may be identical in size to flasks presently used, and the flange 36 does not increase the plan dimension of the unit, which would diminish the number of flasks that could be placed in an incubator.

In the embodiment of FIGS. 4–6, most of the features described in connection with the preferred embodiment are found, and the corresponding parts are identified by primed numbers. Thus, the base of the flask composed of the bottom wall 10', side walls 12' and 14', end walls 16' and 18', and neck 22' are identical to those of the first embodiment. The cover 20', however, differs from the cover 20 of the earlier embodiment, in that the opening 34 is larger than the opening 34, which has the advantage of providing easier access to the full surface 30 of panel 28. It will be noted particularly in FIGS. 5 and 6 that the opening 34' extends very close to the end wall 16' so that the flange 36 in top wall 20' adjacent end wall 16' is substantially smaller than the corresponding flange in the first embodiment. Consequently, the media fill line 48' as shown in FIG. 6 lies above the edge 34A of opening 34' and the media M comes in contact with the flexible plastic cover 38'. This arrangement is desirable as it provides more complete access to the growing surface of the bottom panel 28.

Figure 7:
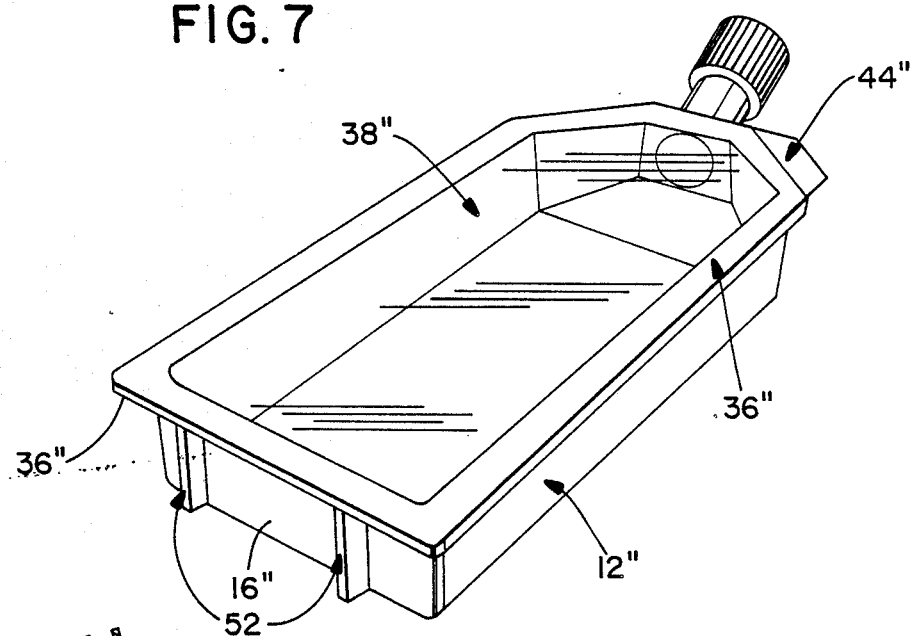
FIG. 7 is a perspective view of yet another embodiment of this invention.
Figure 8:
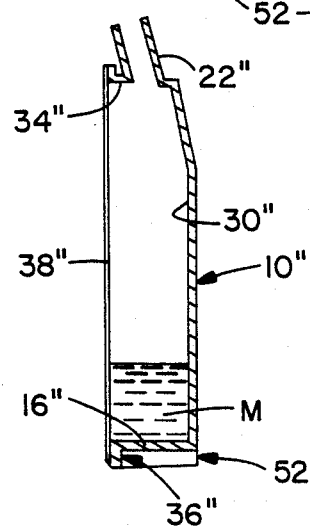
FIG. 8 is cross-sectional view through the flask of FIG. 7 with the cover removed, and showing the flask standing on end in position for filling.

FIGS. 7 and 8 illustrate yet another embodiment of this invention. Unlike the embodiments of FIGS. 1–3 and 4–6, the flask of this embodiment may be molded in a single piece and no ultrasonic welding of separately molded parts is required. In this embodiment, the base not only includes the bottom wall 10", side walls 12" and 14", end walls 16" and 18", and neck 22" but the flange 36" as well. The flange 36" serves as the top wall of the flask and it defines the opening 34" which affords complete access to the surface 30" of bottom wall 10. Cover 38" like the covers of the other embodiments may be heat sealed or attached by pressure sensitive adhesive to the flange 36".

While the embodiment of FIGS. 7 and 8 has the advantage of enabling the flask to be molded as one piece and eliminates the need for ultrasonic welding, the flange 36" essentially increases the plan dimensions of the flask so that fewer such flasks may be placed in a given incubator. Furthermore, this embodiment places the media in contact with the flexible plastic cover 38" during filling as shown in FIG. 8. In addition, this particular design requires that feet 52 be provided on the end wall 16" so as to enable the flask to stand on end for filling as in FIG. 8. The feet 52, of course, must be at least as high as the flange 36" so as to allow the flask to stand erect. The advantage, as stated, is that it may be molded as a single piece and eliminates the need for ultrasonic welding as part of the manufacturing process.

From the foregoing description, the advantages of the present invention over the prior art will be fully appreciated. Each of the configurations provides very easy access to the full horizontal growing surface of the bottom wall of the flask when the cover is removed. In presently available prior art tissue culture flasks, the only access to the growing surface without breaking the flask is through the neck, and various techniques have been devised such as disclosed in copending application Ser. No. 06/825,442 filed Feb. 3, 1986 entitled Laboratory Flask and assigned to the assignee of the present invention to improve access to the surface through the neck. The present invention which allows access to the growing surface is particularly useful in growing monolayers of skin cells and for tumor research. In growing artificial skin, the user would typically desire to lift the monolayer of epithelial cells off the surface in sheets for application to the patient's body. The large access opening to the surface allows the large segments of skin cells to be readily removed. It will be appreciated that this is not possible without breaking the flask when the only access to the interior is through the neck. In tumor research, a particular area of the growing surface may be harvested for further analysis. This cannot conveniently be done through the neck of the flask. With access to the entire surface with the cover removed, a scraper used to harvest cells may very easily and coveniently reach any area desired.

Having described this invention in detail, those skilled in the art will appreciate that numerous modifications may be made thereof without departing from its spirit. Therefore, it is not intended that the breadth of this invention be limited to the specific embodiments illustrated and described. Rather, it is intended that the scope of this invention be determined by the appended claims and their equivalents.

What is claimed is:

1. A tissue culture flask comprising
    a bottom wall having a flat tissue culture growing surface,
    side and end walls extending upwardly from the bottom wall,
    an open neck adapted to receive a removable cover connected to one of the end walls,
    a top wall generally parallel to the growing surface,
    an opening in the top wall exposing a substantial portion of the growing surface,
    and a transparent cover attached to the top wall about the opening and being peelable from the top wall to enable the user to gain access to the growing surface, said cover being disposed to overlap a portion of said top wall, said top wall and said cover being attached at said overlapping portion.

2. A tissue culture flask as defined in claim 1 wherein the bottom wall is an optical surface permitting distortion free viewing of the tissue cultures growing on the surface through the bottom wall.

3. A tissue culture flask as defined in claim 1 wherein the bottom and top walls are separately molded and ultrasonically welded together.

4. A tissue culture flask as defined in claim 1 wherein a flange surrounds the opening in the top wall, said flange being said overlapping portion, and the periphery of the cover is heat sealed to the flange when the opening is closed.

5. A tissue culture flask as defined in claim 4 wherein the bottom, side and end walls are molded as a unit of a transparent plastic material.

6. A tissue culture flask as defined in claim 4 wherein the cover is a flexible transparent plastic film.

7. A tissue culture flask comprising
a bottom wall having a flat tissue culture growing surface,
side and end walls extending upwardly from the bottom wall,
an open neck adapted to receive a removable cover connected to one of the end walls,
a top wall including a flange defining an opening in the top wall for access to the growing surface,
a cover separate from the top wall and attached to the flange and closing the opening, said cover overlapping said flange,
and means for removing the cover wall from the flange to provide access to the surface.

8. A tissue culture flask comprising
rigid plastic top, bottom and side walls secured together to define a chamber,
a first opening in one of said walls for introducing media and other substances into the chamber,
said bottom wall being transparent, said wall providing a tissue culture growing surface,
a second opening in the top wall spaced inwardly from the periphery of said top wall and a flange in the top wall surrounding said opening,
and a flexible clear plastic closure sheet overlapping the flange and secured to the flange about the second opening and peelable therefrom for closing the opening.

9. A tissue culture flask as defined in claim 8 wherein a pull tab is connected to the closure sheet for removing the sheet from the top wall.

10. A tissue culture flask as defined in claim 8 wherein a recess is provided under the margin of the sheet to facilitate gripping of the sheet to peel it off the top wall.

11. A tissue culture flask as defined in claim 8 wherein the first opening is defined by a neck secured to one of the side walls,
one of the other of the side walls being disposed opposite the side wall to which the neck is attached and providing a stand for the flask for supporting the flask on a surface when media is poured into the flask.

12. A tissue culture flask as defined in claim 11 wherein
the flange in the top wall adjacent the side wall providing the stand being sufficiently wide so that the media poured into the flask while the flask is supported on the stand does not reach the second opening.

13. A tissue culture flask as defined in claim 8 wherein the flange extends beyond the side walls.

14. A tissue culture flask comprising rigid plastic top and bottom walls connected together by sides, an open neck adapted to receive a removable cover connected to one of the sides said bottom wall having an inner surface for growing tissue cultures,
an opening in the top wall opposite the inner surface of the bottom wall for access to said surface,
and a cover secured to the top wall for closing the opening, said cover overlapping said top wall at a portion of said top wall.

15. A tissue culture flask as defined in claim 14 wherein
the cover is made of a flexible transparent plastic film sealed to said portion of said top wall and being peelable therefrom.

* * * * *